(12) United States Patent
Knochel et al.

(10) Patent No.: US 6,284,925 B1
(45) Date of Patent: Sep. 4, 2001

(54) USE OF FERROCENYL LIGANDS FOR CATALYTIC, ENANTIOSELECTIVE HYDROGENATION

(75) Inventors: Paul Knochel; Juan Jose Almena Perea, both of Marburg; Karlheinz Drauz, Freigericht; Ingo Klement, Pohlheim, all of (DE)

(73) Assignee: Degussa-Huls AG, Hanau (DE)

( * ) Notice: Subject to any disclaimer, the term of this patent is extended or adjusted under 35 U.S.C. 154(b) by 0 days.

(21) Appl. No.: 09/335,894

(22) Filed: Jun. 18, 1999

(30) Foreign Application Priority Data

Jun. 19, 1998 (DE) ............................... 198 27 311
May 12, 1999 (DE) ............................... 199 21 924

(51) Int. Cl.[7] .......................... C07B 53/00; C07C 227/32
(52) U.S. Cl. .......................... 564/415; 554/143; 554/145; 556/18; 585/260
(58) Field of Search ..................... 564/415, 422; 554/145, 143; 556/18; 585/260; 568/814

(56) References Cited

U.S. PATENT DOCUMENTS

| | | | |
|---|---|---|---|
| 5,371,256 | * 12/1994 | Tongi et al. | ............................... 556/14 |
| 5,859,300 | * 1/1999 | Jalett et al. | ............................... 564/143 |
| 6,008,393 | * 12/1999 | Sablong et al. | ........................ 556/18 |

FOREIGN PATENT DOCUMENTS

02062886 * 8/1998 (JP).
0967015 A * 8/1998 (EP).

OTHER PUBLICATIONS

Schwink et al., New $C_2$–Symmetrical Ferrocenyl Diamines as Ligands for Ruthenium Catalyzed Transfer Hydrogenation, Tetrahedron: Asymmetry 9, 1998, pp. 1143–1149.
Hayashi et al., A New Chiral Ferrocenylphosphine Ligand with $C_2$ Symmetry: Preparation and Use for Palladium–Catalysed Asymmetric Cross–Coupling, J. Chem. Soc., Chem. Commun., 1989, pp. 495–496.

Togni et al., A Novel Easily Accessible Chiral Ferrocenyldiphosphine for Highly Enantioselective Hydrogenation, Allylic Alkylation, Hydroboration Reactions, J. Am. Chem. Soc., 1994, 116, pp. 4062–4066.
Hayashi et al., Catalytic Asymmetric Hydrogenation of β–Disubstituted α–Phenylacrylic Acids Asymmetric Synthesis of Carboxylic Acids Containing Two Vicinal Chiral Carbon Centers, Tetrahedron Letters, vol. 29, No. 46, 1988, pp. 5969–5972.
Perea et al., Synthesis and Application of $C_2$–Symmetric Diamino Ferriphos as Ligands for Enantioselective RH–Catalyzed Preparation of Chiral α–Amino Acids, Tetrahedron: Asymmetry 10, 1999, pp. 375–384.

* cited by examiner

Primary Examiner—Bekir L. Yildirim
(74) Attorney, Agent, or Firm—Pillsbury Winthrop LLP

(57) ABSTRACT

The use of the ligands and complexes of general formula I and II for catalytic, enantioselective hydrogenation.

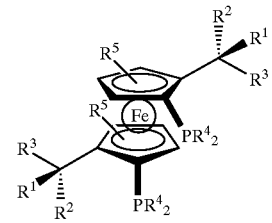

(I)

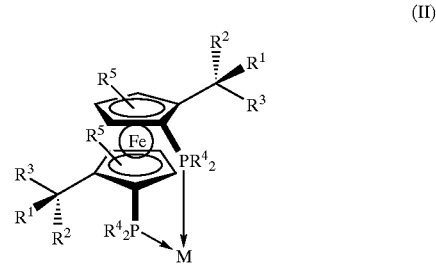

(II)

10 Claims, No Drawings

USE OF FERROCENYL LIGANDS FOR CATALYTIC, ENANTIOSELECTIVE HYDROGENATION

CROSS-REFERENCE TO RELATED APPLICATIONS

This application claims priority from German Applications No. 198 27 311.8, filed on Jun. 19, 1998 and 199 21 924.9 filed on May 12, 1999, the subject matter of each of which is hereby incorporated herein by reference.

BACKGROUND OF THE INVENTION

1. Field of the Invention

The present invention relates to the use of enantiomer-enriched ligands of the general formula I and their salts

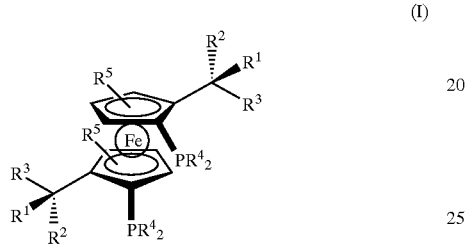

(I)

in which $R^1$, $R^2$, $R^3$ signify, independently of each other, H, $NR^6R^7$, $SR^6$, $(C_1-C_8)$-alkyl, $(C_1-C_8)$-alkoxy, $(C_2-C_8)$-alkoxyalkyl, $(C_1-C_8)$acyloxy, which can be optionally present as linear or branched and can be substituted singly or multiply with halogens, with groups containing N, O, P, S atoms, $(C_3-C_7)$-cycloalkyl, which can be substituted singly or multiply with linear or branched $(C_1-C_8)$-alkyl, which can be optionally substituted singly or multiply with halogens, groups containing N, O, P, S atoms, with halogens, with groups containing N, O, P, S atoms and/or can contain heteroatoms such as N, O, P, S in the ring such as 1-, 2-, 3-, 4-piperidyl, such as 1-, 2-, 3-pyrrolidinyl, 2-, 3-tetrahydrofuryl, 2-, 3-, 4-morpholinyl, $(C_6-C_{18})$-aryl, such as phenyl, 1-, 2-naphthyl or anthryl, $(C_6-C_{18})$-aralkyl, such as benzyl or 1,1-, 1,2-phenethyl, $(C_5-C_{18})$-heteroaryl, such as 2-, 3-furyl, 2-, 3-pyrrolyl, 2-, 3-, 4-pyridyl, $(C_6-C_{18})$-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups can optionally be substituted singly or multiply with linear or branched $(C_1-C_8)$-alkyl, $(C_1-C_8)$-acyl, $(C_1-C_8)$-alkoxy, $(C_2-C_8)$-alkoxyalkyl, which can be substituted singly or multiply with halogens, groups containing N, O, P, S atoms, with halogens, with groups containing N, O, P, S atoms, or $R^1$ and $R^2$ are joined in a $(C_3-C_7)$-carbocycle which can be substituted singly or multiply with linear or branched $(C_1-C_8)$-alkyl, $(C_1-C_8)$-acyl, $(C_1-C_8)$-alkoxy, $(C_2-C_8)$-alkoxyalkyl, which can optionally be substituted singly or multiply with halogens, groups containing N, O, P, S atoms, with halogens, with groups containing N, O, P, S atoms and/or can contain heteroatoms such as N, O, P, S in the ring, $R^4$ signifies $(C_1-C_8)$-alkyl, $(C_6-C_{18})$-aryl, such as phenyl, 1-, 2-naphthyl, 2,2'-biphenyl or anthryl,1-pyrrolyl, and the just-cited groups can be optionally substituted with linear or branched $(C_1-C_8)$-alkyl, $(C_1-C_8)$-alkoxy, $(C_2-C_8)$-alkoxyalkyl, which can be substituted singly or multiply with halogens, groups containing N, O, P, S atoms, with halogens, with groups containing N, O, P, S atoms, $(C_3-C_7)$-cycloalkyl, which can be singly or multiply substituted with linear or branched $(C_1-C_8)$-alkyl, $(C_1-C_8)$-alkoxy, $(C_2-C_8)$-alkoxyalkyl, which can be optionally substituted singly or multiply with halogens, groups containing N, O, P, S atoms, with halogens, with groups containing N, O, P, S atoms and/or can contain heteroatoms such as N, O, P, S in the ring, $R^5$ signifies H or a group B—X—Z in which B is a group selected from $CR^8_2$, $NR^8$, O, S, and $SiR^8_2$, X is a spacer such as, e.g., 1,4'-biphenyl, 1-, 2-ethylene, 1-, 3-propylene, PEG-(2-10) and Z is a group bound to a polymer via a functional group such as, e.g., the O—, NH—, COO—, CONH—, ethenyl—, NHCONH—, OCONH— or NHCOO— function, or the groups $R^5$ of the two cyclopentadienyl rings are connected to each other via an α, ω-$(C_2-C_4)$-alkylene bridge, $R^6$, $R^7$ signify, independently of one another, H, $(C_1-C_8)$-alkyl, $(C_1-C_8)$-alkoxy, $(C_2-C_8)$-alkoxyalkyl, $(C_1-C_8)$-acyl, which are optionally linear or branched and can be singly or multiply substituted with halogens, with groups containing N, O, P, S atoms, $(C_3-C_7)$-cycloalkyl, which can be substituted singly or multiply with linear or branched $(C_1-C_8)$-alkyl, $(C_1-C_8)$-acyl, $(C_1-C_8)$-alkoxy, $(C_2-C_8)$-alkoxyalkyl, which can be optionally substituted singly or multiply with halogens, groups containing N, O, P, S atoms, with halogens, with groups containing N, O, P, S atoms and/or can contain heteroatoms such as N, O, P, S in the ring such as 1-, 2-, 3-, 4-piperidyl, such as 1,2-, 3-pyrrolidinyl, 2-, 3-tetrahydrofuryl, 2-, 3-, 4-morpholinyl, $(C_6-C_{18})$-aryl, such as phenyl, 1-, 2-naphthyl or anthryl, $(C_6-C_{18})$-aralkyl, such as benzyl or 1,1-, 1,2-phenethyl, $(C_5-C_{18})$-heteroaryl, such as 2-, 3-furyl, 2-, 3-pyrrolyl, 2-, 3-, 4-pyridyl, $(C_6-C_{18})$-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups can optionally be substituted singly or multiply with linear or branched $(C_1-C_8)$-alkyl, $(C_1-C_8)$-acyl, $(C_1-C_8)$-alkoxy, $(C_2-C_8)$-alkoxyalkyl, which can be substituted singly or multiply with halogens, groups containing N, O, P, S atoms, with halogens, with groups containing N, O, P, S atoms, or $R^6$ and $R^7$ are joined in a $(C_3-C_7)$ carbocycle, which can be substituted singly or multiply with linear or branched $(C_1-C_8)$-alkyl, $(C_1-C_8)$-acyl, $(C_1-C_8)$-alkoxy, $(C_2-C_8)$-alkoxyalkyl, which can optionally be substituted singly or multiply with halogens, groups containing N, O, P, S atoms, with halogens, with groups containing N, O, P, S atoms, and/or can contain heteroatoms such as N, O, P, S in the ring, and $R^8$ signifies H, $(C_1-C_8)$-alkyl for homogeneous, catalytic, enantioselective hydrogenation.

Moreover, the invention concerns the use of enantiomer-enriched complexes of the general formula II and their salts

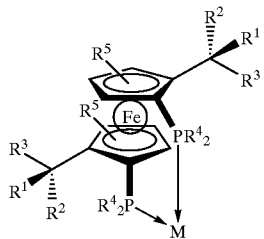

(II)

in which
R¹ to R⁸ have the meanings indicated above and M is a metal atom or metal ion of the subgroup [B group] 8, e.g., Ni, Co, Rh, Ru, Ir, Pd, Re or Pt for enantioselective, homogeneous, catalytic hydrogenation.

2. Background Information

The homogeneous, catalytic, enantioselective hydrogenation of imines and enamines is of great interest for the production of, e.g., amino acids enriched with enantiomers since the latter are required for their part as chiral educts in the organic synthesis, e.g., of bioactive active substances.

The use of bisphosphine catalysts for the enantioselective, homogeneous, catalytic hydrogenation for the purpose just cited is well known (Burk et al., Tetrahedron 1994, 4399).

Hayashi et al. (J. Chem. Soc., Chem Commun. 1989, 495–496), Knochel et al. (Chem. Eur. J. 1998, 4, 950–968) and Ikeda et al. (Tetrahedron Lett. 1996, 4545–4548) describe Pd complexes with $C_2$-symmetric ferrocenyl-(bistertiary phosphine) ligands. However, these complexes were used solely in asymmetric allylations and cross couplings. The use of ligands in enantioselective hydrogenation was not known up to the present.

Yamamoto at al. (Bull. Chem. Soc. Jpn. 1980, 53, 1132–1137) reported about the use of non $C_2$-symmetric ferrocenyl-(bis-tertiary phosphine) ligands in enantioselective, homogeneous, catalytic hydrogenation. However, good excesses of enantiomers are obtained only very sporadically with these ligands.

SUMMARY OF THE INVENTION

It is therefore an object of the present invention to provide a method using $C_2$-symmetric, enantiomer-enriched bisphosphine ligand systems and -catalysts for the homogeneous, enantioselective, catalytic hydrogenation of multiple bonds.

The term "multiple bonds" denotes in the framework of the invention double bonds between a carbon atom and another carbon atom or nitrogen atom.

As a result of the fact that the enantiomer-enriched ligands of the general formula I and their salts are used for the homogeneous, catalytic, enantioselective hydrogenation of multiple bonds,

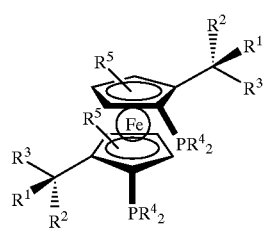

(I)

in which
R¹, R², R³ signify, independently of each other, H, $NR^6R^7$, $SR^6$, halogen, $(C_1–C_8)$-alkyl, $(C_1–C_8)$-alkoxy, $(C_2–C_8)$-alkoxyalkyl, $(C_1–C_8)$-acyloxy, which can be optionally present as linear or branched as well as can be substituted singly or multiply with halogens, with groups containing N, O, P, S atoms, $(C_3–C_7)$-cycloalkyl, which can be substituted singly or multiply with linear or branched $(C_1–C_8)$-alkyl, which can be optionally substituted singly or multiply with halogens, groups containing N, O, P, S atoms, with halogens, with groups containing N, O, P, S atoms and/or can contain heteroatoms such as N, O, P, S in the ring such as 1-, 2-, 3-, 4-piperidyl, such as 1-, 2-, 3-pyrrolidinyl, 2-, 3-tetrahydrofuryl, 2-, 3-, 4-morpholinyl, $(C_6–C_{18})$-aryl, such as phenyl, 1-, 2-naphthyl or anthryl, $(C_6–C_{18})$-aralkyl, such as benzyl or 1,1-, 1,2-phenethyl, $(C_5–C_{18})$-heteroaryl, such as 2-, 3-furyl, 2-, 3-pyrrolyl, 2-, 3-, 4-pyridyl, $(C_6–C_{18})$-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups can optionally be substituted singly or multiply with linear or branched $(C_1–C_8)$-alkyl, $(C_1–C_8)$-acyl, $(C_1–C_8)$-alkoxy, $(C_2–C_8)$-alkoxyalkyl, which can be substituted singly or multiply with halogens, groups containing N, O, P, S atoms, with halogens, with groups containing N, O, P, S atoms, or R¹ and R² are joined in a $(C_3–C_7)$-carbocycle which can be substituted singly or multiply with linear or branched $(C_1–C_8)$-alkyl, $(C_1–C_8)$-acyl, $(C_1–C_8)$-alkoxy, $(C_2–C_8)$-alkoxyalkyl, which can optionally be substituted singly or multiply with halogens, groups containing N, O, P, S atoms, with halogens, with groups containing N, O, P, S atoms and/or can contain heteroatoms such as N, O, P, S in the ring, R⁴ signifies $(C_1–C_8)$-alkyl, $(C_6–C_{18})$-aryl, such as phenyl, 1-, 2-naphthyl, 2,2'-biphenyl or anthryl,1-pyrrolyl, and the just-cited groups can be optionally substituted with linear or branched $(C_1–C_8)$-alkyl, $(C_1–C_8)$-alkoxy, $(C_2–C_8)$-alkoxyalkyl, which can be substituted singly or multiply with halogens, groups containing N, O, P, S atoms, with halogens, with groups containing N, O, P, S atoms, $(C_3–C_7)$-cycloalkyl, which can be singly or multiply substituted with linear or branched $(C_1–C_8)$-alkyl, $(C_1–C_8)$-alkoxy, $(C_2–C_8)$-alkoxyalkyl, which can be optionally substituted singly or multiply with halogens, groups containing N, O, P, S atoms, with halogens, with groups containing N, O, P, S atoms and/or can contain heteroatoms such as N, O, P, S in the ring, R⁵ signifies H or a group B—X—Z in which B is a residue of the group $CR^8_2$, $NR^8$, O, S, $SiR^8_2$, X is a spacer such as, e.g., 1,4'-biphenyl, 1-, 2-ethylene, 1-, 3-propylene, PEG-(2-10) and Z is a group bound to a polymer via a functional group such as, e.g., the O—, NH—, COO—, CONH—, ethenyl-, NHCONH—, OCONH— or NHCOO— function, or the groups R⁵ of the two cyclopentadienyl rings are connected to each other via an α, ω-$(C_2–C_4)$-alkylene bridge, R⁶, R⁷ signify, independently of one another, H, $(C_1–C_8)$-alkyl, $(C_1–C_8)$-alkoxy, $(C_2–C_8)$-alkoxyalkyl, $(C_1–C_8)$-acyl, which are linear or branched and can be singly or multiply substituted with halogens, with groups containing N, O, P, S atoms, $(C_3–C_7)$-cycloalkyl, which can be substituted singly or multiply with linear or branched $(C_1–C_8)$-alkyl, ($C_1$–$C_8$)-acyl, ($C_1$–$C_8$)-alkoxy, ($C_2$–$C_8$)-alkoxyalkyl, which can be optionally substituted singly or multiply with halogens, groups containing N, O, P, S atoms, with halogens, with groups containing N, O, P, S atoms and/or can contain heteroatoms such as N, O, P, S in the ring such as 1-, 2-, 3-, 4-piperidyl, such as 1, 2-, 3-pyrrolidinyl, 2-, 3-tetrahydrofuryl, 2-, 3-, 4-morpholinyl, ($C_6$–$C_{18}$)-aryl, such as phenyl, 1-, 2-naphthyl or anthryl, ($C_6$–$C_{18}$)-aralkyl, such as benzyl or 1,1-, 1,2-phenethyl, ($C_5$–$C_{18}$)-heteroaryl, such as 2-, 3-furyl, 2-, 3-pyrrolyl, 2-, 3-, 4-pyridyl, ($C_6$–$C_{18}$)-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups can optionally be substituted singly or multiply with linear or branched ($C_1$–$C_8$)-alkyl, ($C_1$–$C_8$)-acyl, ($C_1$–$C_8$)-alkoxy, ($C_2$–$C_8$)-alkoxyalkyl, which can be substituted singly or multiply with halogens, groups containing N, O, P, S atoms, with halogens, with groups containing N, O, P, S atoms, or $R^6$ and $R^7$ are joined in a ($C_3$–$C_7$) carbocycle, which can be substituted singly or multiply with linear or branched ($C_1$–$C_8$)-alkyl, ($C_1$–$C_8$)-acyl, ($C_1$–$C_8$)-alkoxy, ($C_2$–$C_8$)-alkoxyalkyl, which can optionally be substituted singly or multiply with halogens, groups containing N, O, P, S atoms, with halogens, with groups containing N, O, P, S atoms, and/or can contain heteroatoms such as N, O, P, S in the ring, and $R^8$ signifies H, ($C_1$–$C_8$)-alkyl, the corresponding hydrogenated derivatives are obtained in very good space/time yields and have a very high ee value.

Ligands of formula I are used with preference, in which $R^1$, $R^2$ signify, independently of one another, H, N ($C_1$–$C_8$)-alkyl$_2$, NH ($C_1$–$C_8$)-acyl, N ($C_1$–$C_8$)acyl$_2$, O ($C_1$–$C_8$)-acyl, ($C_1$–$C_8$)-alkyl, ($C_1$–$C_8$)-alkoxy, ($C_2$–$C_8$)-alkoxyalkyl, which can be linear or branched, ($C_3$–$C_7$)-cycloalkyl, ($C_6$–$C_{18}$)-aryl, such as phenyl, 1-, 2-naphthyl or anthryl, $R^3$ signifies ($C_3$–$C_7$)-cycloalkyl, ($C_6$–$C_{18}$)-aryl, such as phenyl, 1-, 2-naphthyl or anthryl and the just-cited groups can optionally be substituted singly or multiply with linear or branched ($C_1$–$C_8$)-alkyl, with halogens, $R^4$ signifies ($C_1$–$C_8$)-alkyl, ($C_3$–$C_7$)-cycloalkyl, ($C_6$–$C_{18}$)-aryl, such as phenyl, 1-, 2-naphthyl or anthryl and the just-cited groups can optionally be singly or multiply substituted with linear or branched ($C_1$–$C_8$)-alkyl, with halogens, and $R^5$ signifies H.

The use of ligands of formula I is especially preferred in which $R^1$, $R^2$ signify, independently of one another, H, O ($C_1$–$C_8$)-acyl, N ($C_1$–$C_8$)-alkyl$_2$, ($C_1$–$C_8$)-alkyl, $R^3$ signifies ($C_6$–$C_{18}$)-aryl, such as phenyl, 1-, 2-naphthyl or anthryl and the just-cited groups can optionally be substituted singly or multiply with linear or branched ($C_1$–$C_8$)-alkyl, with halogens, $R^4$ signifies phenyl, $R^5$ signifies H.

A further aspect of the invention concerns the use of enantiomer-enriched complexes of general formula II and their salts

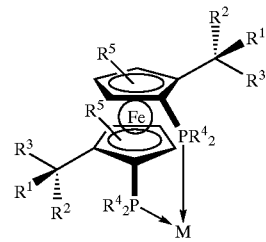

(II)

in which $R^1$ to $R^8$ have the meanings indicated above and M is a metal atom or metal ion of subgroup 8, e.g., Co, Ni, Rh, Ru, Ir, Pd, Re, for the homogeneous, catalytic, enantioselective hydrogenation of C═C and C═N double bonds. The coordination sites of central atom M left free in the general formula for the complex (II) in accordance with the invention and indicated above are ligands known to the expert in the art for this reaction (R. Schrock, J. A. Osborn, J. Am. Chem. Soc. 1971, 93, 2397–2407; R. Glaser, S. Geresh, J. Blumenfeld, J. Organomet. Chem. 1976, 112, 355–360) or possibly fill out the solvent present during the reaction. The coordinators are to be imagined for the corresponding formula (II).

The use, in accordance with the invention, of the ligands and complexes is superior to comparable hydrogenations in the state of the art. Thus, the complexes exhibit such a high activity for the reaction considered and such a pronouncedly low sensitivity to oxidation by atmospheric oxygen that in contrast to comparable catalysts of the state of the art the degassing and the use of p.A. solvents can be eliminated. Solvent of industrial quality is sufficient for use during the hydrogenation.

Once again, the use of the complexes of formula II is preferred in which $R^1$, $R^2$ signify, independently of one another, H, N ($C_1$–$C_8$)alkyl$_2$, NH ($C_1$–$C_8$)-acyl, N ($C_1$–$C_8$)-acyl$_2$, O ($C_1$–$C_8$)-acyl, ($C_1$–$C_8$)-alkyl, ($C_1$–$C_8$)-alkoxy, ($C_2$–$C_8$)-alkoxyalkyl, which are linear or branched, ($C_3$–$C_7$)-cycloalkyl, ($C_6$–$C_{18}$)-aryl, such as phenyl, 1-, 2-naphthyl or anthryl, $R^3$ signifies ($C_3$–$C_7$)-cycloalkyl, ($C_6$–$C_{18}$)-aryl, such as phenyl, 1-, 2-naphthyl or anthryl and the just-cited groups can optionally be substituted singly or multiply with linear or branched ($C_1$–$C_8$)-alkyl, with halogens, $R^4$ signifies ($C_1$–$C_8$)-alkyl, ($C_3$–$C_7$)-cycloalkyl, ($C_6$–$C_{18}$)-aryl, such as phenyl, 1-, 2-naphthyl or anthryl and the just-cited groups can optionally be singly or multiply substituted with linear or branched ($C_1$–$C_8$)-alkyl, with halogens, $R^5$ signifies H.

The use of ligands of formula II is quite especially preferred in which $R^1$, $R^2$ signify, independently of one another, H, O ($C_1$–$C_8$)-acyl, N ($C_1$–$C_8$)-alkyl$_2$, ($C_1$–$C_8$)-alkyl, $R^3$ signifies ($C_6$–$C_{18}$)-aryl, such as phenyl, 1-, 2-naphthyl or anthryl and the just-cited groups can optionally be substituted singly or multiply with linear or branched ($C_1$–$C_8$)-alkyl, with halogens, $R^4$ signifies phenyl, $R^5$ signifies H.

The complexes which can be produced from the ligand systems exhibit excellent values in the homogeneous, enantioselective, catalytic hydrogenation, as the following tables document.

TABLE 1

Ph-CH=C(COOR)(N(H)Ac) + 1% Rh(COD)₂BF₄ + 1% Ligand → (H₂) → Ph-CH₂-CH(COOR)(N(H)Ac)

| Ligand | R | ee (%) |
|---|---|---|
| [Ferrocene ligand with Me/Ph CH groups and PPh₂] | Me | 98.6 |
| dito | H | 97.3 |
| [Ferrocene ligand with Me/o-Tolyl CH groups and PPh₂] | Me | 98.1 |
| dito | H | 97.6 |
| [Ferrocene ligand with Me/2-Naphthyl CH groups and PPh₂] | Me | 98.6 |
| dito | H | 97.3 |

TABLE 2

R'-CH=C(COOR'')(N(H)Ac) + 1% Rh(nbd)₂BF₄ + 1% [Ferrocene ligand with Me/Ph CH groups and PPh₂] → (H₂, rt) → R'-CH₂-CH(COOR'')(N(H)Ac)

| R' | R'' | ee (%) |
|---|---|---|
| H | H | 98.0 |
| H | Me | 97.9 |
| Ph | H | 97.5 |
| Ph | Me | 98.5 |
| Ph | Me | 98.4[a] |
| 2-Naphthyl | Me | 98.3 |

TABLE 2-continued

[Reaction scheme: alkene with COOR″ and N(H)Ac groups + 1% Rh(nbd)₂BF₄ + 1% ferrocene-based ligand (with Me, Ph, PPh₂ substituents), H₂, rt → chiral product with COOR″ and N(H)Ac groups]

| R' | R" | ee (%) |
|---|---|---|
| 2-Naphthyl | Me | 99.4[b] |
| 2-Naphthyl | H | 98.2 |

[a]MeOH as solvent without preceding degassing
[b]Reaction temperature −14° C.

TABLE 3

[Reaction scheme: alkene with COOR″ and N(H)Ac groups + 1% Rh(nbd)₂BF₄ + 1% ferrocene-based ligand (with Ph, PPh₂ substituents), H₂, rt → chiral product]

| R' | R" | ee (%) |
|---|---|---|
| Ph | Me | 97.4 |
| 2-Naphthyl | Me | 95.8 |
| 2-Naphthyl | H | 95.3 |

TABLE 4

[Reaction scheme: alkene with COOMe and N(H)Ac groups + 1% Rh(nbd)₂BF₄ + 1% ferrocene-based ligand (with NR'R″, Ph, PPh₂ substituents), H₂, rt → chiral product with COOMe and N(H)Ac groups]

| R | R' | R" | ee (%) |
|---|---|---|---|
| Ph | Me | Me | 97.4 |
| 2-Naphthyl | Me | Me | 95.8 |
| Ph | —(CH₂)₄— | | 97.7 |
| Ph | Me | Cyclohexyl | 97.8 | nbd is the abbreviation for 2,5-norbornadiene, COD stands for 1,5-cyclooctadiene.

The reaction time for the reactions shown above is <60 min. The concentration of catalyst is already very low with 1% in the examples cited. However, it can be lowered significantly for industrial use. These two facts are very advantageous for the use of the ligands in accordance with the invention on an industrial scale since the expenses for the products obtained according to this method are correspondingly lower and a greater economical use is guaranteed therewith than when using ligand systems/complexes of the state of the art. This advantage is conditioned by the expressly good activity of the ligand systems and ligand complexes.

In addition thereto, the ligand systems are so insensitive to oxidation that they can be preserved unchanged for a long time under ambient conditions. This is also advantageous for storage on a large scale.

The production of the ligand systems is described in the state of the art (Knochel et al., Chem. Eur. J. 1998, 4, 950 ff.; Enders et al., Syn. Lett. 1997, 355f.; Knochel et al., Tetrahedron Lett. 1996, 37, 25ff.; Schmalz et al., Tetrahedron 1997, 53, 7219ff.). A survey shows other possible synthesis paths (Scheme 1).

in the art for this reaction (J. Am. Chem. Soc. 1957, 79, 2742; J. Organomet. Chem. 1973, 52, 407–424). However, the reduction with the so-called CBS reagent is preferred (J. Am. Chem. Soc. 1987, 109, 5551–5553; Tetrahedron Lett. 1996, 37, 25–28). This measure assures that the reduction products accumulate in very good yields and with a very

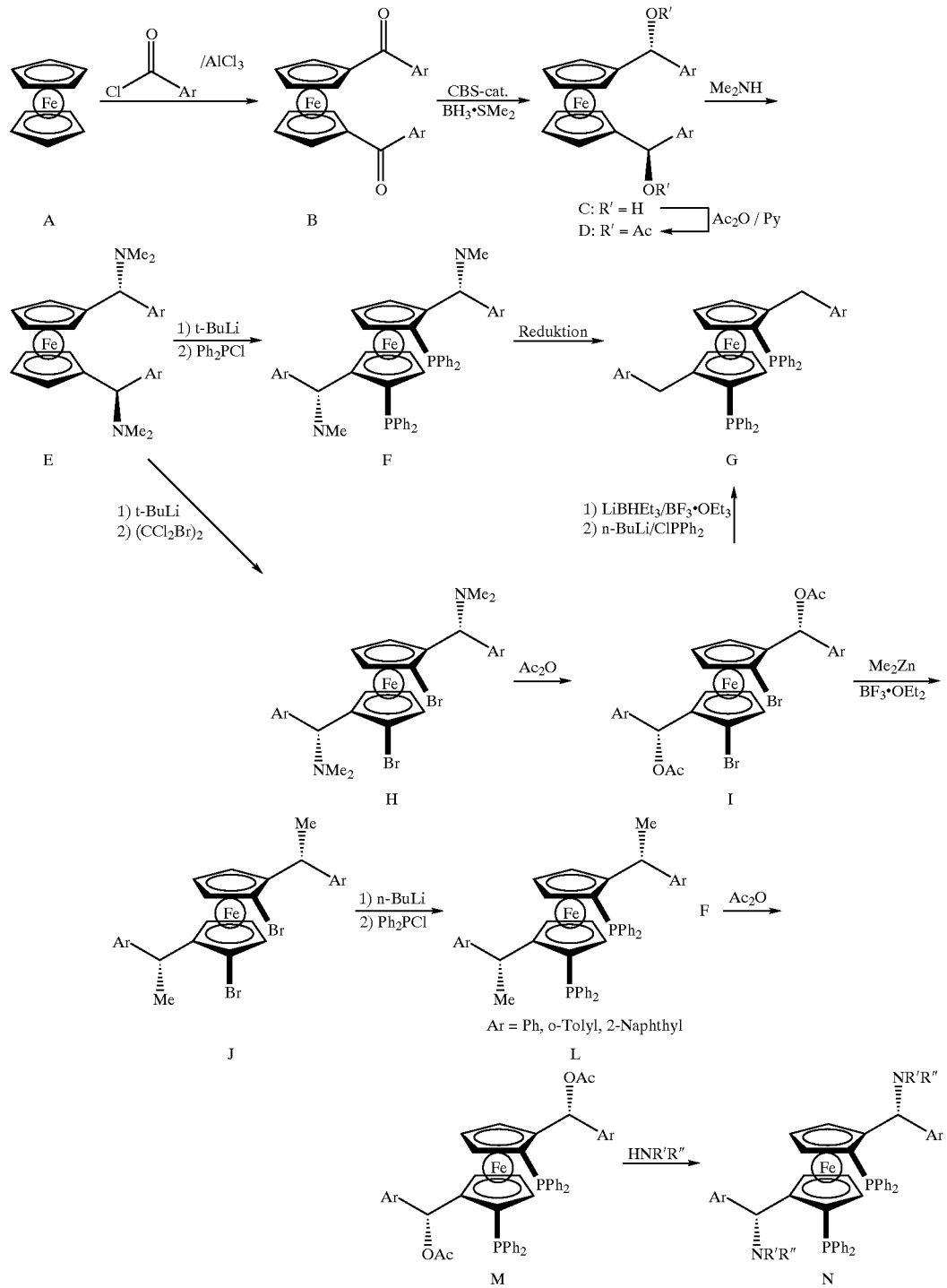

The introduction of a preferred central and planar chirality into the 1,1-diacylated ferrocene can take place in principle according to all methods which are known to those of skill in the art high optical and diastereomeric purity. A further conceivable path for producing desired enantiomer-enriched ligands can be seen, e.g., in the producing of the 1,1'-diacylated ferrocenes by means of enantioselective, reductive amination. This yields the enantiomer-enriched ligands at once with an amine substituent on the stereogenic center.

Further possibilities for the introduction of chirality are described in principle in Tetrahedron Asymmetry 1991, 2, 601–612; J. Org. Chem. 1991, 56, 1670–1672; J. Org. Chem. 1994, 59, 7908–7909; J. Chem. Soc., Chem. Commun. 1990, 888–889.

In order to introduce the $R^5$ group the acidic protons on the ring can be deprotonized in a deprotonization step and the deprotonized species subsequently reacted with a suitable electrophilic reagent for the introduction of an $R^5$ group.

The $R^5$ group can, among other things, be used to bond the complexes of the invention to a polymeric matrix such as, e.g., a linear PMMA, polystyrene or PEG as well as to a non-linear dendrimer. The bonding of the $R^5$ group to the cyclopentadienyl ring of the complex of the invention is variable as regards the free positions. All groups known to those of skill in the art for this purpose can be used as groups. A suitable survey for the molecular enlargement of complex catalysts is found in Tetrahedron Asymmetry 1998, 9, 691–696. The $R^5$ group preferably consists of the arrangement B—X—Z in which B is a residue of a group $CR^8_2$, $NR^8$, O, S, or $SiR^8_2$, X is a spacer such as, e.g., 1,4'-biphenyl, 1-, 2-ethylene, 1-, 3-propylene, PEG-(2-10) and Z is a group bound to a polymer like the one described above via a functional group such as, e.g., the O—, NH—, COO—, CONH—, ethenyl-, NHCONH—, OCONH— or NHCOO— function. Alternatively, the $R^5$ groups of the two cyclopentadienyl rings can be connected to each other via an α, ω-$(C_2-C_4)$-alkylene bridge.

Methyl, ethyl, n-propyl, isopropyl, n-butyl, isobutyl, sec-butyl, tert-butyl, pentyl, hexyl, heptyl or octyl together with all of their bonding isomers can be considered as linear or branched $(C_1-C_8)$- or $(C_2-C_8)$alkyl groups. The $(C_1-C_8)$-alkoxy group corresponds to the $(C_1-C_8)$-alkyl group, provided that the latter is connected to the molecule via an oxygen atom. $(C_2-C_8)$-alkoxyalkyl denotes groups in which the alkyl chain is interrupted by at least one oxygen function and two oxygen atoms can not be connected to one another thereby. The number of carbon atoms indicates the total number of carbon atoms contained in the group. Groups containing N, O, P, S atoms are in particular alkyl groups of the type cited above which comprise one or several of these heteroatoms in their chain and which are bound to the molecule via one of these heteroatoms. $(C_3-C_7)$-cycloalkyl denotes cyclopropyl, cyclobutyl, cyclopentyl, cyclohexyl and cycloheptyl groups.

$(C_1-C_8)$-acyloxy signifies in the framework of the invention an alkyl group defined as above which is bound to the molecule via a COO function.

$(C_1-C_8)$-acyl signifies in the framework of the invention an alkyl group defined as above which is bound to the molecule via a CO function.

Halogens include fluorine, chlorine, bromine and iodine.

The term "salts" denotes ionic addition compounds of strong acids such as HCl, HBr, $H_2SO_4$, $H_3PO_4$, $CF_3COOH$, p-toluene sulfonic acid, methane sulfonic acid and the considered molecule.

PEG signifies polyethylene glycol.

DETAILED DESCRIPTION OF THE INVENTION

The following examples are intended to explain the invention.

EXAMPLES

General Method of Procedure

All reactions were carried out under argon unless otherwise indicated. The workup of the reaction mixtures took place as follows: Hydrolysis with saturated $NH_4Cl$ solution, extraction with methyl-tert.-butylether (MTBE) (3×10 ml), washing of the combined organic extracts with saturated NaCl solution (20 ml), drying over $MgSO_4$, filtration, evaporation to low bulk of the filtrates in a vacuum and purification of the residues by column chromatography with silica gel 60 (70–230 mesh ASTM) and different compositions of mixtures of hexane/MTBE. Melting points are uncorrected.

The methanol used had been previously dried over Mg and distilled under argon as well as degassed with argon. HPLC methanol was used without previous purification. It turned out that HPLC methanol can also be replaced by industrial methanol which has not been worked up.

1. General Directions for the Production of 1,1'-diacylferrocenes by Friedel-Crafts Acylation (A->B)

Acetylchloride is added to a suspension of aluminum(III) chloride in $CH_2Cl_2$(10 ml) at 0° C. The ferrocene is subsequently added, dissolved in 10 ml $CH_2Cl_2$, dropwise to this mixture within 20 min. The reaction mixture is heated to room temperature and agitated 2 h. The mixture is subsequently hydrolyzed dropwise with ice water at 0° C. The mixture is diluted with 100 ml methylene chloride, washed twice with aqueous $K_2CO_3$ solution (50 ml) and then washed with saturated NaCl solution (50 ml). The organic phase is dried and concentrated. The residue is purified by column chromatography.

1,1'-Dibenzoylferrocene: The solid is obtained from ferrocene (13.95 g, 75.0 mmol), benzoylchloride (19.2 ml, 165.0 mmol) and aluminum(III) chloride (22.00 g, 165.0 mmol) in a yield of 91% (27.1 g, 68.3 mmol) after crystallization out of pentane; red solid m.p. 97–100° C. (lit. 106.5–106.7° C.); IR (KBr): $V_{max}$=3267(w), 3113(w), 3064 (w), 1637(vs), 1448(s), 1288(s), 1048(m), 846(m), 726(s), 698(s).

1,1'-Di(o-toluoyl)ferrocene: The solid is obtained from ferrocene (1.43 g, 7.7 mmol), o-toluoylchloride (2.11 mL, 16.2 mmol) and aluminum(III) chloride (2.16 g, 16.2 mmol) in a yield of 73% (2.36 g, 5.6 mmol) after purification with column chromatography; red solid m.p. 124–125° C.; IR (KBr): $V_{max}$=3085(w), 2923(w), 1647(vs), 1443(m), 1273 (s), 840(m), 737(s).

1,1'-Di(2-naphthoyl)ferrocene: A solid is obtained from ferrocene (1.86 g, 10.0 mmol), 2-naphthoylchloride (4.2 g, 22.0 mmol) and aluminum(III) chloride (3.5 g, 26.0 mmol) after purification with column chromatography in a yield of 35% (1.72 g, 3.48 mmol); red solid m.p. 183–184° C.; IR (KBr): $V_{max}$=3100(w), 3055(w), 1642(vs), 1447(m), 1294 (s), 810(m), 778(s), 757(m).

2. General Directions for Carrying Out the CBS Reduction of 1,1'-diacylferrocenes (B->C)

Oxazaborolidine is dissolved under argon (according to J. Am. Soc. 1987, 109, 5551–5553) (60 molar %) in THF (5 mL) and cooled to 0° C. Then, 2 eq. $BH_3$•$SMe_2$ are dissolved in THF (5 mL) and 20% of this solution added to the catalytic solution. After 5 min residual $BH_3$•$SMe_2$ and a solution of diketone in THF (10 mL) are added simultaneously to the catalytic solution. After 10 min agitation at 0° C. the excess $BH_3$•$SMe_2$ is destroyed by the addition of methanol (2 mL). The mixture is then placed in saturated $NH_4Cl$ solution (50 mL) and extracted with MTBE (3×25 mL). The combined organic phases are washed with water (2×25 mL) and saturated NaCl solution (100 mL), dried, concentrated and purified by column chromatography.

(R,R)-1,1'-bis(α-hydroxyphenylmethyl) ferrocene: The corresponding diketone (11.82 g, 30.0 mmol) is brought to reaction with oxazaborolidine (4.98 g, 18.0 mmol) and $BH_3$•$SMe_2$(5.7 mL, 60.0 mmol). The desired product dl:meso=96:4 is obtained after column chromatography in 89% yield (10.62 g, 26.3 mmol). Crystallization out of MTBE yields a yellow solid dl:meso=98:2; ee>99%; m.p.

130–132° C.; $[\alpha]_D$=–74.3(c=0.97, benzene); IR (KBr): $V_{max}$=3526(vs), 3081(w), 3026(w), 1491(m), 1452(m), 1049(m), 1017(m), 828(m), 721(s), 699(s).

(R,R)-1,1'-bis(α-hydroxy-o-tolylmethyl)ferrocene: The corresponding diketone (4.22 g, 10.0 mmol) is reduced with oxazaborolidine (1.66 g, 6.0 mmol) and BH$_3$•SMe$_2$(1.90 mL, 20.0 mmol) and then purified by column chromatography. A yellow solid (4.01 g, 9.4 mmol) is obtained in 94% yield; dl:meso=97:3; ee>99%; m.p. 138° C.; $[\alpha]_D$=–46.3(c=0.67, CHCl$_3$); IR (KBr): $V_{max}$=3270(vs), 3077(w), 2926(w), 1043(s), 820(m), 738(s).

(R,R)-1-1'-bis[α-hydroxy-(2-naphthyl) methyl] ferrocene: The corresponding diketone (996 mg, 2.00 mmol) is reduced with oxazaborolidine (332 mg, 1.20 mmol) and BH$_3$•SMe$_2$(4.0 ml), 1M in THF) and then purified by column chromatography. A yellow solid (793 mg, 1.59 mmol) is obtained in 80% yield; dl:meso=97:3; ee>99%; m.p. 187–188° C.; $[\alpha]_D$=+61.5(c=0.63, THF); IR (KBr): $V_{max}$=3380(s), 3053(w) 2863(w), 1054(m), 1017(m), 786 (m), 751(m).

3. General production of the acetates (C->D)

The ferrocene diols are dissolved in a mixture of pyridine/acetane hydride 2:1 and left for 12 h at RT. Then, evaporable constituents are distilled off in a vacuum (0.7 mm Hg, 5 h). The products are sufficiently pure and are used without further purification.

(R,R)-1,1'-bis(α-acetoxyphenylmethyl)ferrocene: Yellow oil dl:meso=93: 7; ee>98%; $[\alpha]_D$=–30.0(c=1.81, CHCl$_3$); IR (neat): $V_{max}$=3089(w), 3066(w), 3035(m), 2937(w), 1733 (vs), 1372(s), 1241(vs), 1019(s), 830(m), 731(s), 700(s).

(R,R)-1,1'-bis(α-acetoxy-o-tolylmethyl) ferrocene: Dark brown oil dl:meso=94:6; ee>98%; $[\alpha]_D$=–57.7(c=0.96, CHCl$_3$); IR (neat): $V_{max}$=3025(w), 2935(s), 1720(vs), 1450 (m), 1365(m), 1225(vs), 1020(m), 820(m), 740(m).

(R,R)-1,1'-bis[α-acetoxy-(2-naphthyl)methyl] ferrocene: Yellow solid dl:meso=84:16; m.p. 129–130° C.; $[\alpha]_D$=–3.5 (c=0.51, CHCl$_3$); IR (KBr): $V_{max}$=3054(w), 2957(w), 1732 (vs), 1373(m), 1233(vs), 1043(m), 1021(m), 788(m), 761 (m).

4. General Working Directions for Reacting Ferrocene Acetates with Dimethylamine in THF/H$_2$O (D->E)

The ferrocene acetates are dissolved in THF. This solution is compounded with a 40% excess of aqueous dimethylamine solution. After agitation for 12 h at RT the reaction mixture is worked up and purified by column chromatography.

(R,R)-1,1'-bis(α-N,N-dimethylaminophenylmethyl) ferrocene: The corresponding diacetate (7.95 g, 16.5 mmol) is reacted with dimethylamine (40% in water 60 mL) in 40 mL THF/10 mL water. The corresponding diamine is obtained as brown oil in 91% yield (6.79 g, 15.0 mmol); dl:meso=96:4; $[\alpha]_D$=+122.0(c=1.36, CHCl$_3$); IR (neat): $V_{max}$=3060(w), 3030(w), 2950(m), 2860 9w), 2810(w), 2770(s), 1455(s), 1300(m), 1005(s), 830(m), 740(s), 700(m).

(R,R)-1,1'-bis(α-N,N-dimethylamino-o-tolylmethyl) ferrocene: The corresponding diacetate (510 mg, 1.00 mmol) is reacted with dimethylamine (40% in water, 4 mL) in 10 mL THF/2.5 mL water. The corresponding diamine is obtained in 81% yield as orange solid (389 mg, 0.81 mmol); dl:meso=85:15; m.p. 104–106° C.; $[\alpha]_D$=+120.1(c=1.29, CHCl$_3$); IR (KBr): $V_{max}$=3064(w), 3020(w), 1602(w), 1006(s), 823(m), 739(vs).

(R,R)-1,1'-bis[α-N,N-dimethylamino-(2-naphthyl) methyl]ferrocene: The corresponding diacetate (1,33 g, 2.28 mmol) is reacted with dimethylamine (40% in water, 20 mL) in 30 mL THF/7.5 mL water. The corresponding diamine is obtained in 88% yield as orange solid (1.10 g, 2.0 mmol); dl:meso=92:8; m.p. 142–143° C.; $[\alpha]_D$=–47.1(c=0.47, CHCl$_3$); IR (KBr): $V_{max}$=3058(w), 2979(w), 2944(w), 2810 (m), 2762(s), 1296(m), 1011(s), 828(s), 762(m).

5. General Directions for Producing the Synthesis of Bromides (E->H)

The corresponding diamines are dissolved in Et$_2$O (5 mL), cooled to 0° C. and compounded with Bu$^t$Li (c=1.5 M; 3 eq) within 5 min. The solution is agitated 30 min at this temperature. Then, a solution of 1,2-dibromotetrachloroethane (3 eq) in Et$_2$O (5 mL) is added within 10 min. The mixture is agitated 3 h at RT, worked up and purified with column chromatography.

(αR, α'R)-2,2'-bis(α-N,N-dimethylaminophenylmethyl)-(S,S)-1,1'-dibromoferrocene: The corresponding diamine (460 mg, 1.00 mmol) is compounded with Bu$^t$Li (2.0 mL, 3.00 mmol) and then with (CBrCl$_2$)$_2$ (977 mg, 3.00 mmol). After purification with column chromatography a dark brown oil is obtained in 80% yield (486 mg, 0.80 mmol) which contains a diastereomer (ee=100%). $[\alpha]_D$=+154.5(c=0.88, CHCl$_3$); IR (neat): $V_{max}$=3084(w), 3063(w), 3026(w), 2816(s), 2772(s), 1601(w), 1491(w), 1009(s), 756(vs), 735 (vs).

(αR, α'R)-2,2'-bis(α-N,N-dimethylamino-o-tolylmethyl)-(S,S)-1,1'-dibromoferrocene: The corresponding diamine (2.16 g, 4.49 mmol) is reacted with Bu$^t$Li (8.9 mL, 13.48 mmol) and (CBrCl$_2$)$_2$(4.39 g, 13.48 mmol). After purification with column chromatography and recrystallization out of diethylether/hexane a brown solid is obtained in 52% yield (1.50 g, 2.35 mmol) which contains a diastereomer (ee=100%). m. p. 169–171° C.; $[\alpha]_D$=+224.2(c=0.78, CHCl$_3$); IR (KBr): $V_{max}$=3071(w), 3046(w), 3021(w), 1601 (w), 823(s), 744(s).

(αR, α'R)-2,2'-bis(α-N,N-dimethylamino-2-naphthylmethyl)-(S,S)-1,1'-dibromoferrocene: The corresponding diamine (0.60 g, 1.09 mmol) is reacted with Bu$^t$Li (2.2 mL, 3.26 mmol) and (CBrCl$_2$)$_2$(1.06 g, 13.48 mmol). After purification with column chromatography and recrystallization out of diethylether/hexane a brown solid is obtained in 43% yield (0.33 g, 0.47 mmol) which contains a diastereomer (ee>98%). Mp: 147–148° C.; $[\alpha]_D$=–49.6(c=0.74, CHCl$_3$); IR (KBr): $V_{max}$=3057(w), 1601(w), 1508(w), 907(s), 824(s), 735(s).

6. General Directions for Producing Dibromoferrocenes (H->I)

The corresponding aminobromides (1 mmol) are dissolved in acetic anhydride (4 mL) and heated to 100° C. for 2.5 h. Then the volatile constituents are removed in a vacuum (0.7 mm Hg, 3 h). The corresponding acetates are obtained in quantitative yield (>95%, NMR).

(αR, α'R)-2,2'-bis(α-acetoxyphenylmethyl)-(S,S)-1,1'-dibromoferrocene: Yellow solid mp: 145–147° C.; $[\alpha]_D$=+83.2(c=0.90, CHCl$_3$); IR (KBr): $V_{max}$=1738(vs), 1225(vs).

(αR, α'R)-2,2'-bis(α-acetoxy-o-tolylmethyl)-(S,S)-1,1'-dibromoferrocene: Yellow solid mp: 143–144° C.; $[\alpha]_D$=+71.5(c=0.92, CHCl$_3$); IR (KBr) 1735(vs), 1231(vs).

(αR, α'R)-2,2'-bis(α-acetoxy-2-naphthylmethyl)-(S,S)-1,1'-dibromoferrocene: Yellow solid mp: 90–93° C.; $[\alpha]_D$=+55.6(c=1.11, CHCl$_3$); IR (KBr): $V_{max}$=3057(w), 3025(w), 1748(vs), 1235(vs).

7. General Directions for Carrying out the Reaction of the Acetates with Organozinc Reagents (I->J)

The organozinc reagents (3 eq) and BF$_3$OEt$_2$(2 eq) are added to a solution of the corresponding acetates in 5 mL dry THF at –78° C. under argon. The reaction mixture is heated to RT within 1.5 h and then worked up after another hour as usual. The raw product is purified by column chromatography.

(αR, α'R)-2,2'-bis(α-methylphenylmethyl)-(S,S)-1,1'-dibromoferrocene: The acetate (219 mg, 0.34 mmol) is compounded with BF$_3$OEt$_2$(84 μL, 0.68 mmol) and dimethyl zinc (neat; 1.03 mmol, 71 μL). A brown oil is obtained in 98% yield (184 mg, 0.33 mmol); ee=100%; $[\alpha]_D$=+171.4 (c=1.10, CHCl$_3$); IR (neat): $V_{max}$=3084(w), 3061(w), 3028 (w), 1601(w), 1584(w), 1493(s), 816(s), 77s (vs), 706 (vs).

(αR, α'R)-2,2'-bis[α-methyl-(o-tolyl)methyl]-(S,S)-1,1'-dibromoferrocene: The acetate (134 mg, 0.20 mmol) is compounded with $BF_3OEt_2$(49 μL, 0.40 mmol) and dimethyl zinc (neat; 0.60 mmol, 41 μL). After column chromatography a brown solid is obtained in 100% yield (116 mg, 0.20 mmol); ee=100%; mp=76–78° C.; $[α]_D$=+118.9(c=0.73, $CHCl_3$); IR (KBr): $V_{max}$=3065(w), 3021(w), 1603(w), 1491(w), 816(s), 758(s).

(αR, α'R)-2,2'-bis[α-methyl-2-naphthylmethyl)-(S,S)-1,1'-dibromoferrocene: The acetate (195 mg, 0.26 mmol) is compounded with $BF_3OEt_2$(65 μL, 0.52 mmol) and dimethyl zinc (neat; 0.79 mmol, 54 μL). After column chromatographic purification a yellow solid is obtained in 92% yield (55 mg, 0.24 mmol); ee=100%; mp=58–60° C.; $[α]_D$=+86.5(c=1.04, $CHCl_3$); IR (KBr): $V_{max}$=3055(w), 3021(w), 1601(w), 1508(w), 820(s), 750(s), 733(s).

8. Synthesis of $C_2$-Symmetric Diphosphines (J->L)

Bu"Li (c=1.50; 3 eq) is added to a solution of THF (5 mL) and the corresponding bromide at −78° C. and the solution then compounded after 15 min with diphenylchlorophosphine (neat; 4 eq). The reaction mixture is heated to RT and agitated 1 h at this temperature before it is worked up according to the customary procedure with column chromatography. After recrystallization from diethylether the $C_2$-symmetric diphosphines are obtained.

(αR, α'R)-2,2'-bis(α-methylphenylmethyl)-(S,S)-1,1'-bis(diphenylphosphino)ferrocene: The corresponding bromide (275 mg, 0.50 mmol) is reacted with Bu"Li (1.00 mL, 1.50 mmol) and $ClPPh_2$(360 μL, 2.00 mmol). After column chromatography and recrystallization from diethylether an orange solid is obtained in 68% yield (263 mg, 0.34 mmol); mp: 181–182° C.; $[α]_D$=−245.2(c=0.40, $CHCl_3$); IR (KBr): $V_{max}$=3056(w), 3026(w), 1600(w), 1583(w), 1493(w), 748 (s), 741(s), 697(vs).

(αR, α'R)-2,2'-bis[α-methyl-(o-tolyl)methyl]-(S,S)-1,1'-bis(diphenylphosphino)ferrocene: The corresponding bromide (100 mg, 0.17 mmol) is reacted with Bu"Li (345 μL, 0.52 mmol) and $ClPPh_2$(120 μL, 0.68 mmol). After column chromatography and recrystallization from diethylether an orange solid is obtained in 64% yield (85 mg, 0.11 mmol); mp: 164–166° C.; $[α]_D$=−402.4(c=0.67, $CHCl_3$); IR (KBr): $V_{max}$=3054(w), 3019(w), 1603(w), 1586(w), 1570(w), 1489 (m), 735(vs), 698(vs).

(αR, α'R)-2,2'-bis[α-methyl-2-naphthylmethyl)-(S,S)-1,1'-bis(diphenylphosphino)ferrocene: The corresponding bromide (300 mg, 0.46 mmol) is reacted with Bu"Li (1.12 mL, 1.680 mmol) and $ClPPh_2$ (330 μL, 1.84 mmol). After column chromatography and recrystallization from diethylether/dichloromethane an orange solid is obtained in 46% yield (184 mg, 0.21 mmol); mp: 208–210° C.; $[α]_D$=−256.3(c=0.54, $CHCl_3$); IR (KBr): $V_{max}$=3052(w), 1601(w), 1584(w), 822(s), 741(s), 689(s).

9. Synthesis of Planar chiral Diphosphinoferrocenes Starting from Acetate (I->G)

The corresponding acetate (174 mg, 0.27 mmol) is dissolved in 5 mL THF and cooled to 0° C. Then $BF_3OEt_2$(2.2 eq, 73 μL, 0.59 mmol) is added dropwise to the mixture. After 15 min a 1 M solution of $LiHBEt_3$ in THF (2.2 eq, 0.59 mmol, 0.59 mL) is added and the mixture left at RT for 3 h. After a normal workup and purification by column chromatography the corresponding dibromide is obtained in 66% yield (93 mg, 0.18 mmol) as a yellow solid.

(S,S)-2,2'-dibenzyl-1,1'-dibromoferrocene: mp: 61–64° C.; $[α]_D$=+81.8(c=1.05, $CHCl_3$); IR (KBr): $V_{max}$=3083(w), 3059(w), 3025 (w), 1601(w), 1582(w), 814(m), 724(m), 707(s), 693(s).

(S,S)-2,2'-dibenzyl-1,1'-bis(diphenylphosphino) ferrocene: The dibromide can be converted into the diphosphine in analogy with the above-cited directions (J->L). To this end the bromide (135 mg, 0.26 immol) is reacted with Bu"Li (510 μL, 0.77 mmol) and $ClPPh_2$(185 μL, 1.03 mmol). After column chromatography a yellow solid is obtained in 66% yield (127 mg, 0.17 mmol); mp: 66–68° C.; $[α]_D$=−329.3(c=1.60, $CHCl_3$); IR (KBr): $V_{max}$=3028(m), 3001(m), 1660(m), 1601(s), 1586(s), 1570(m), 741(vs), 696 (vs).

10. Synthesis of Diaminodiphosphine Ferrocenes (C->F)

The corresponding diamines (2.40 g, 5.3 mmol) are reacted following directions 5 with Bu'Li (10.6 mL, 15.9 mmol) and $ClPPh_2$(3.8 mL, 21.2 mmol). After column chromatographic purification a yellow solid is obtained in 49% yield (2.14 g, 2.6 mmol) which contains a diastereomer (ee>99%).

(αR, α'R)-2,2'-bis(α-N,N-dimethylaminophenylmethyl)-(S,S)-1,1'-bis(diphenylphosphino) ferrocene: mp: 245–246° C.; $[α]_D$=−330.3° (c=1.00, $CHCl_3$); IR (KBr): $V_{max}$=3090 (w), 3064(w), 3030(w), 2951 (m), 2856(w), 2811(m), 2764 (s), 1450(s), 1006(s), 814(m), 737(s), 703(s) $cm^{-1}$.

11, General Directions for Producing the Synthesis of Diacetate Diphosphine Ferrocene (F->M)

The corresponding diamino diphosphine ferrocenes (1 mmol) are dissolved in acetic anhydride (4 mL) following directions 6 and heated to 100° C. for 2.5 h. Then the volatile constituents are removed in a vacuum (0.7 mm Hg, 3 h). A yellow solid is obtained in quantitative yield (>95 %, NMR) which contains a diastereomer (ee>99%).

(αR, α'R)-2,2'-bis(α-acetoxyphenylmethyl)-(S,S)-,1,1'-bis(diphenylphosphino)ferrocene: mp: 184° C. (decomposition); $[α]_D$=−169.6(c=0.46, $CHCl_3$).

12. General Working Directions for Reacting Diamino Diphosphine Ferrocenes with Various Amines in $CH_3CN$/$H_2O$ (M->N)

Diacetate diphosphine ferrocene is dissolved in $CH_3CN$. This solution is compounded with 50 equivalents of the corresponding amines and heated to 90° C. for 12 h. The reaction mixture is worked up and purified by column chromatography.

(αR, α'R)-2,2'-bis(α-pyrrolidine phenylmethyl)-(S,S)-1,1'-bis(diphenylphosphino)ferrocene: The corresponding diacetate (0.30 g, 0.35 mmol) is reacted with pyrrolidine (1.46 mL, 17.5 mmol) in 2 mL $CH_3CN$/0.2 mL water. The corresponding diamine is obtained as orange solid in 65% yield after column chromatographic purification and recrystallization from diethylether/hexane: mp: 242° C. (decomposition); $[α]_D$=−317.5(c=0.53, $CHCl_3$); IR (KBr): $n_{max}$=3067(w), 3024(w), 1601(w), 1585(w), 737(s), 698(s).

(αR, α'R)-2,2'-bis[α-(N-methyl-N-cyclohexylamino)-phenylmethyl ]-(S,S)-1,1'-bis(diphenylphosphino) ferrocene: The corresponding diacetate (0.16 g, 0.18 mmol) is reacted with N-methyl-N-cyclohexylamine (1.20 mL, 9.3 mmol) in 2 mL $CH_3CN$/0.2 mL water. The corresponding diamine is obtained as yellow solid in 87% yield after column chromatographic purification and recrystallization from [out of] hexane: mp: 224° C. (decomposition); $[α]_D$=−290.2(c=0.57, $CHCl_3$); IR (KBr): $n_{max}$=3071(w), 3053(w), 3001(w), 1600(w), 1111584(w), 741(s), 701(s).

13. Hydrogenation of (Z)-Methyl-β-(2-naphthyl)-α-Acetamido Acrylates $[Rh(nbd)_2]BF_4$ complex (3.7 mg, 0.01 mol) is placed in a dry 50 ml shaker vessel under argon and the corresponding ligand (0.01 mol), dissolved in 8 mL MeOH (HPLC purity or industrial quality), added. Within 15 to 30 min the diphosphine has dissolved. A solution of 2 mL MeOH and (Z)-methyl-β-(2-naphthyl)-α-acetamido acrylate (0.269 g, 1 mmol) is added and then a balloon flask filled with $H_2$(approximately 1.0 bar) is connected to the system. After rinsing the system with $H_2$ the $H_2$ balloon flask is removed after agitation for a further 10 min and the MeOH drawn off in a vacuum. The residue is purified on silica gel with column chromatography. The desired product is obtained in quantitative yield.

(R)-methyl-3-(2-naphthyl)-2-acylamido propanoate: Oil; $[α]_D$=−104.3(c=0.92, $CHCl_3$; ee=99.4%) [Lit: +97.8 (c=1, CHCl$_3$)]; The spectroscopic data agree with the data from the literature (J. Am. Chem. Soc. 1993, 115, 10125–10138).

14. Hydrogenation of (Z)-β-(2-Naphthyl)-α-Acetamidoacrylic Acid (Usual Method)

The same procedure is used as was described for the corresponding esters. The corresponding acid (0.255 g, 1 mmol) is hydrogenated 10 min. Then the MeOH is removed in a vacuum and 5 mL dry ether and 5 mL dry MeOH added to the residue. Then 2 equivalents of Me$_3$SiCHN$_2$ (c=2 M; 1.0 mL, 2.0 mmol) are added dropwise to the reaction mixture. After 1 h the solvent is removed in a vacuum and the residue treated and analyzed in as in the case described above.

(R)-methyl-3-(2-naphthyl)-2-acylamido propanoates: Oil; [α]$_D$=−104.3(c=0.92, CHCl$_3$; ee=98.2%) [Lit: +97.8 (c=1, CHCl$_3$)]. The spectroscopic data agree with the data from the literature (J. Am. Chem. Soc. 1993, 115, 10125–10138).

References and patents cited herein are hereby incorporated by reference.

What is claimed is:

1. A method for the homogeneous, catalytic, enantioselective hydrogenation of C=C and C=N double bonds comprising using an enantiomer-enriched ligand of general formula I, or salt thereof

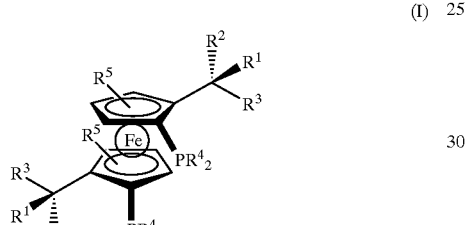

(I)

in which

R$^1$, R$^2$, R$^3$ signify, independently of each other, H, NR$^6$R$^7$, SR$^6$, (C$_1$–C$_8$)-alkyl, (C$_1$–C$_8$)-alkoxy, (C$_2$–C$_8$)-alkoxyalkyl, (C$_1$–C$_8$)acyloxy, which are linear or branched and may be substituted singly or multiply with halogens, with groups containing N, O, P, S atoms, (C$_3$–C$_7$)-cycloalkyl, which may be substituted singly or multiply with linear or branched (C$_1$–C$_8$)-alkyl, which may be optionally substituted singly or multiply with halogens, groups containing N, O, P, S atoms, with halogens, with groups containing N, O, P, S atoms and/or may contain heteroatoms such as N, O, P, S in the ring such as 1-, 2-, 3-, 4-piperidyl, such as 1-, 2-, 3-pyrrolidinyl, 2-, 3-tetrahydrofuryl, 2-, 3-, 4-morpholinyl, (C$_6$–C$_{18}$)-aryl, such as phenyl, 1-, 2-naphthyl or anthryl, (C$_6$–C$_{18}$)-aralkyl, such as benzyl or 1,1-, 1,2-phenethyl, (C$_5$–C$_{18}$)-heteroaryl, such as 2-, 3-furyl, 2-, 3-pyrrolyl, 2-, 3-, 4-pyridyl, (C$_6$–C$_{18}$)-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups may optionally be substituted singly or multiply with linear or branched (C$_1$–C$_8$)-alkyl, (C$_1$–C$_8$)-acyl, (C$_1$–C$_8$)-alkoxy, (C$_2$–C$_8$)-alkoxyalkyl, which may be substituted singly or multiply with halogens, groups containing N, O, P, S atoms, with halogens, with groups containing N, O, P, S atoms, or R$^1$ and R$^2$ are joined in a (C$_3$–C$_7$)-carbocycle which can be substituted singly or multiply with linear or branched (C$_1$–C$_8$)-alkyl, (C$_1$–C$_8$)-acyl, (C$_1$–C$_8$)-alkoxy, (C$_2$–C$_8$)-alkoxyalkyl, which may optionally be substituted singly or multiply with halogens, groups containing N, O, P, S atoms, with halogens, with groups containing N, O, P, S atoms and/or can contain heteroatoms such as N, O, P, S in the ring, R$^4$ signifies (C$_1$–C$_8$)-alkyl, (C$_6$–C$_{18}$)-aryl, such as phenyl, 1-, 2-naphthyl, 2,2'-biphenyl or anthryl,1-pyrrolyl, and the just-cited groups may be optionally substituted with linear or branched (C$_1$–C$_8$)-alkyl, (C$_1$–C$_8$)-alkoxy, (C$_2$–C$_8$)-alkoxyalkyl, which may be substituted singly or multiply with halogens, groups containing N, O, P, S atoms, with halogens, with groups containing N, O, P, S atoms, (C$_3$–C$_7$)-cycloalkyl, which may be singly or multiply substituted with linear or branched (C$_1$–C$_8$)-alkyl, (C$_1$–C$_8$)-alkoxy, (C$_2$–C$_8$)-alkoxyalkyl, which can be optionally substituted singly or multiply with halogens, groups containing N, O, P, S atoms, with halogens, with groups containing N, O, P, S atoms and/or can contain heteroatoms such as N, O, P, S in the ring, R$^5$ signifies H or a group B—X—Z in which B is a residue selected from the group consisting of CR$^8$$_2$, NR$^8$, O, S, and SiR$^8$$_2$, X is a spacer selected from the group consisting of 1,4'-biphenyl, 1-, 2-ethylene, 1-, 3-propylene, and PEG-(2-10) and Z is a group bound to a polymer via a functional group selected from O—, NH—, COO—, CONH—, ethenyl-, NHCONH—, OCONH— and NHCOO—, or the groups R$^5$ of the two cyclopentadienyl rings are connected to each other via an α, ω-(C$_2$–C$_4$)-alkylene bridge, R$^6$, R$^7$ signify, independently of one another, H, (C$_1$–C$_8$)-alkyl, (C$_1$–C$_8$)-alkoxy, (C$_2$–C$_8$)-alkoxyalkyl, (C$_1$–C$_8$)-acyl, which are linear or branched and may be singly or multiply substituted with halogens, with groups containing N, O, P, S atoms, (C$_3$–C$_7$)-cycloalkyl, which may be substituted singly or multiply with linear or branched (C$_1$–C$_8$)-alkyl, (C$_1$–C$_8$)-acyl, (C$_1$–C$_8$)-alkoxy, (C$_2$–C$_8$)-alkoxyalkyl, which may optionally be substituted singly or multiply with halogens, groups containing N, O, P, S atoms, with halogens, with groups containing N, O, P, S atoms and/or may contain heteroatoms such as N, O, P, S in the ring such as 1-, 2-, 3-, 4-piperidyl, such as 1,2-, 3-pyrrolidinyl, 2-, 3-tetrahydrofuryl, 2-, 3-, 4-morpholinyl, (C$_6$–C$_{18}$)-aryl, such as phenyl, 1-, 2-naphthyl or anthryl, (C$_6$–C$_{18}$)-aralkyl, such as benzyl or 1,1-, 1,2-phenethyl, (C$_5$–C$_{18}$)-heteroaryl, such as 2-, 3-furyl, 2-, 3-pyrrolyl, 2-, 3-, 4-pyridyl, (C$_6$–C$_{18}$)-heteroaralkyl, such as furfuryl, pyrrolylmethyl, pyridylmethyl, 1-, 2-furylethyl, 1-, 2-pyrrolylethyl, 1-, 2-pyridylethyl, which aryl, aralkyl, heteroaryl or heteroaralkyl groups may optionally be substituted singly or multiply with linear or branched (C$_1$–C$_8$)-alkyl, (C$_1$–C$_8$)-acyl, (C$_1$–C$_8$)-alkoxy, (C$_2$–C$_8$)-alkoxyalkyl, which may be substituted singly or multiply with halogens, groups containing N, O, P, S atoms, with halogens, with groups containing N, O, P, S atoms, or R$^6$ and R$^7$ are joined in a (C$_3$–C$_7$) carbocycle, which may be substituted singly or multiply with linear or branched (C$_1$–C$_8$)-alkyl, (C$_1$–C$_8$)-acyl, (C$_1$–C$_8$)-alkoxy, (C$_2$–C$_8$)-alkoxyalkyl, which may optionally be substituted singly or multiply with halogens, groups containing N, O, P, S atoms, with halogens, with groups containing N, O, P, S atoms, and/or can contain heteroatoms such as N, O, P, S in the ring, and $R^8$ signifies H, $(C_1–C_8)$-alkyl.

2. The method according to claim 1, wherein $R^1$, $R^2$ signify, independently of one another, H, N $(C_1–C_8)$-alkyl$_2$, NH $(C_1–C_8)$-acyl, N $(C_1–C_8)$acyl$_2$, O $(C_1–C_8)$-acyl, $(C_1–C_8)$-alkyl, $(C_1–C_8)$-alkoxy, $(C_2–C_8)$-alkoxyalkyl, which are linear or branched, $(C_3–C_7)$-cycloalkyl, $(C_6–C_{18})$-aryl, $R^3$ signifies $(C_3–C_7)$-cycloalkyl, $(C_6–C_{18})$-aryl, which may optionally be substituted singly or multiply with linear or branched $(C_1–C_8)$-alkyl, with halogens, $R^4$ signifies $(C_1–C_8)$-alkyl, $(C_3–C_7)$-cycloalkyl, $(C_6–C_{18})$-aryl, which may optionally be singly or multiply substituted with linear or branched $(C_1–C_8)$-alkyl, with halogens, and $R^5$ signifies H.

3. The method according to claim 2, wherein $R^1$ or $R^2$ is phenyl, 1-, 2-naphthyl or anthryl, which may optionally be substituted singly or multiply with linear or branched $(C_1–C_8)$-alkyl and/or with halogens.

4. The method according to claim 2 wherein $R^3$ is phenyl, 1-, 2-naphthyl or anthryl, which may optionally be substituted singly or multiply with linear or branched $(C_1–C_8)$-alkyl and/or with halogens.

5. The method according to claim 2 wherein $R^4$ is phenyl, 1-, 2-naphthyl or anthryl, which may optionally be substituted singly or multiply with linear or branched $(C_1–C_8)$-alkyl and/or with halogens.

6. The method according to claim 2, wherein $R^1$, $R^2$ signify, independently of one another, H, O $(C_1–C_8)$-acyl, N $(C_1–C_8)$-alkyl$_2$, $(C_1–C_8)$-alkyl, $R^3$ signifies $(C_6–C_{18})$-aryl, which may optionally be substituted singly or multiply with linear or branched $(C_1–C_8)$-alkyl, with halogens, $R^4$ signifies phenyl, $R^5$ signifies H.

7. The method according to claim 6, wherein $R^3$ is phenyl, 1-, 2-naphthyl or anthryl, which may optionally be substituted singly or multiply with linear or branched $(C_1–C_8)$-alkyl and/or with halogens.

8. A method for the homogeneous, catalytic, enantioselective hydrogenation of C=C and C=N double bonds comprising using enantiomer-enriched complexes of general formula II and their salts

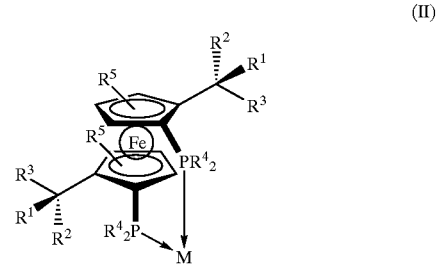

(II)

in which $R^1$ to $R^8$ have the significance indicated in claim 1 and M is a metal atom or metal ion of subgroup 8, e.g., Co, Ni, Rh, Ru, Ir, Pd, Re or Pt.

9. The method according to claim 8, wherein $R^1$, $R^2$ signify, independently of one another, H, N $(C_1–C_8)$-alkyl$_2$, NH $(C_1–C_8)$-acyl, N $(C_1–C_8)$acyl$_2$, O $(C_1–C_8)$-acyl, $(C_1–C_8)$-alkyl, $(C_1–C_8)$-alkoxy, $(C_2–C_8)$-alkoxyalkyl, which are linear or branched, $(C_3–C_7)$-cycloalkyl, $(C_6–C_{18})$-aryl, $R^3$ signifies $(C_3–C_7)$-cycloalkyl, $(C_6–C_{18})$-aryl, which may optionally be substituted singly or multiply with linear or branched $(C_1–C_8)$-alkyl, with halogens, $R^4$ signifies $(C_1–C_8)$-alkyl, $(C_3–C_7)$-cycloalkyl, $(C_6–C_{18})$-aryl, which may optionally be singly or multiply substituted with linear or branched $(C_1–C_8)$-alkyl, with halogens, and $R^5$ signifies H.

10. The method according to claim 9, wherein $R^1$, $R^2$ signify, independently of one another, H, O $(C_1–C_8)$-acyl, N $(C_1–C_8)$-alkyl$_2$, $(C_1–C_8)$-alkyl, $R^3$ signifies $(C_6–C_{18})$-aryl, which may optionally be substituted singly or multiply with linear or branched $(C_1–C_8)$-alkyl, with halogens, $R^4$ signifies phenyl, $R^5$ signifies H.

* * * * *